(12) United States Patent
Reeves et al.

(10) Patent No.: US 8,511,468 B2
(45) Date of Patent: Aug. 20, 2013

(54) SURGICAL INSTRUMENT HOLDER

(75) Inventors: Christopher L. Reeves, Atlanta, GA (US); Markyia S. Nichols, Owings Mills, MD (US)

(73) Assignee: Nichols-Reeves Enterprises, LLC, Lewis, DE (US)

( * ) Notice: Subject to any disclaimer, the term of this patent is extended or adjusted under 35 U.S.C. 154(b) by 347 days.

(21) Appl. No.: 12/710,052

(22) Filed: Feb. 22, 2010

(65) Prior Publication Data

US 2010/0217246 A1    Aug. 26, 2010

Related U.S. Application Data

(60) Provisional application No. 61/154,014, filed on Feb. 20, 2009.

(51) Int. Cl.
*A47F 7/00*    (2006.01)
*B65D 83/10*    (2006.01)

(52) U.S. Cl.
USPC ........ 206/370; 211/70.6; 248/176.1; 206/818

(58) Field of Classification Search
USPC ........ 206/370, 305, 350, 818, 363; 211/70.6; 248/176.1
See application file for complete search history.

(56) References Cited

U.S. PATENT DOCUMENTS

| | | | | |
|---|---|---|---|---|
| 3,696,920 A * | 10/1972 | Lahay | ........................... | 206/370 |
| 4,497,412 A * | 2/1985 | Labelle | ........................ | 211/70.7 |
| 5,005,710 A * | 4/1991 | Hofer | ........................... | 211/70.6 |
| 5,046,624 A * | 9/1991 | Murphy et al. | .............. | 211/70.6 |
| 5,137,151 A * | 8/1992 | Choate | ........................... | 206/370 |
| 5,201,430 A * | 4/1993 | Artzer | ........................... | 211/70.6 |
| 5,505,316 A * | 4/1996 | Lee | .............................. | 211/70.6 |
| 5,681,539 A * | 10/1997 | Riley | ............................. | 422/300 |
| 5,988,382 A * | 11/1999 | Ritchie et al. | ................. | 206/372 |
| 6,047,824 A * | 4/2000 | Winnard | ....................... | 206/350 |
| 6,155,439 A * | 12/2000 | Draughn | .................... | 211/85.13 |
| 6,230,888 B1 * | 5/2001 | Frieze et al. | ................. | 206/370 |
| 6,367,637 B1 * | 4/2002 | Davis et al. | ................ | 211/85.13 |
| 6,969,498 B1 * | 11/2005 | Riley | ............................. | 422/300 |
| 7,070,050 B2 * | 7/2006 | Faller et al. | ................... | 206/380 |
| 7,389,870 B2 * | 6/2008 | Slappay | ........................ | 206/305 |
| 7,886,908 B2 * | 2/2011 | Farrar et al. | ................... | 206/370 |
| 8,069,998 B2 * | 12/2011 | Thomas | ...................... | 211/85.13 |
| D657,460 S * | 4/2012 | Uhlenkamp et al. | ......... | D24/128 |
| 2001/0035384 A1 * | 11/2001 | Davis et al. | ................ | 211/85.13 |
| 2002/0185459 A1 * | 12/2002 | Dietrich | ........................ | 211/70.6 |
| 2005/0040066 A1 * | 2/2005 | Pulsifer | ......................... | 206/438 |
| 2005/0234405 A1 * | 10/2005 | Dikeman et al. | .............. | 604/180 |
| 2006/0070903 A1 * | 4/2006 | Chiang | ......................... | 206/378 |
| 2006/0076254 A1 * | 4/2006 | Corbitt et al. | ................. | 206/370 |
| 2007/0074985 A1 * | 4/2007 | Evans | ........................... | 206/376 |

* cited by examiner

*Primary Examiner* — Jacob K Ackun

(74) *Attorney, Agent, or Firm* — Thomas|Horstemeyer, LLP

(57) ABSTRACT

Disclosed are various embodiments for holding and organizing surgical instruments in a surgical environment. In one embodiment, a surgical instrument holder comprises an elongated body portion including a plurality of slots. Each of the slots may be configured so as to retain a surgical instrument in a fixed position. The elongated body portion may have a base surface configured to contact a table surface.

34 Claims, 3 Drawing Sheets

SURGICAL INSTRUMENT HOLDER

CROSS REFERENCE TO RELATED APPLICATIONS

This Patent Application claims priority to U.S. Provisional Patent Application No. 61/154,014 filed on Feb. 20, 2009 entitled "Surgical Instrument Holder," which is incorporated herein by reference in its entirety.

BACKGROUND

Patient safety is a measurable and improvable outcome in any hospital. Patient outcomes during surgery are continually examined, and there are measurable circumstances which have been shown to improve these outcomes. Studies have shown that a decrease in surgical time and blood loss leads to a decrease in length of hospital stay, decrease in infections, and increased patient satisfaction. Currently, operating room technicians store surgical instruments on rolled towels, decreasing accessibility and visibility of the instruments. Handling of the instruments is also technically difficult with this setup as multiple instruments become attached to one another or mixed with other types of instruments.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

SUMMARY

Briefly described, one embodiment, among others, is a surgical instrument holder. The surgical instrument holder comprises an elongated body portion, which includes a plurality of slots. Each of the slots is configured so as to retain a surgical instrument in a fixed position. The elongated body portion has a base surface configured to contact a table surface.

Another embodiment is also a surgical instrument holder. The surgical instrument holder comprises an elongated body portion having a top surface and a base surface. The base surface is configured to contact a table surface. When a portion of a surgical instrument is laid upon the top surface, the top surface is configured to deform under an applied weight so as to limit movement of the surgical instrument.

Another embodiment is yet another surgical instrument holder. The surgical instrument holder comprises an elongated body portion having a top surface and a base surface. The base surface is configured to contact a table surface. The top surface has a slot formed along a longitudinal axis. The slot is configured to receive a plurality of surgical instruments and to retain each of the surgical instruments in a fixed position.

Another embodiment is a method for organizing surgical instruments in a surgical environment. The method comprises the step of placing a surgical instrument holder upon a table surface. A base surface of the surgical instrument holder thereby fully contacts the table surface and resists movement along the table surface. The method also comprises the step of inserting a first surgical instrument into a first groove in the surgical instrument holder. The first surgical instrument is retained in a fixed position within the first groove. The method also comprises the step of inserting a second surgical instrument into a second groove in the surgical instrument holder. The second surgical instrument is retained in a fixed position within the second groove. The first groove is separated from the second groove by at least one other groove.

Other embodiments of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

DETAILED DESCRIPTION

It is imperative to have a surgical instrument storage system which allows very easy access to as well as rapid access to surgical instruments during a case. The surgical instrument holder of this disclosure meets all of the fundamental requirements of sterile surgical technique and packing, while allowing for quicker instrument counts and easier access during the operation or procedure. This in turn, will lead to decreased surgical time, decreased blood loss, and overall improved patient outcomes.

Figure 1:
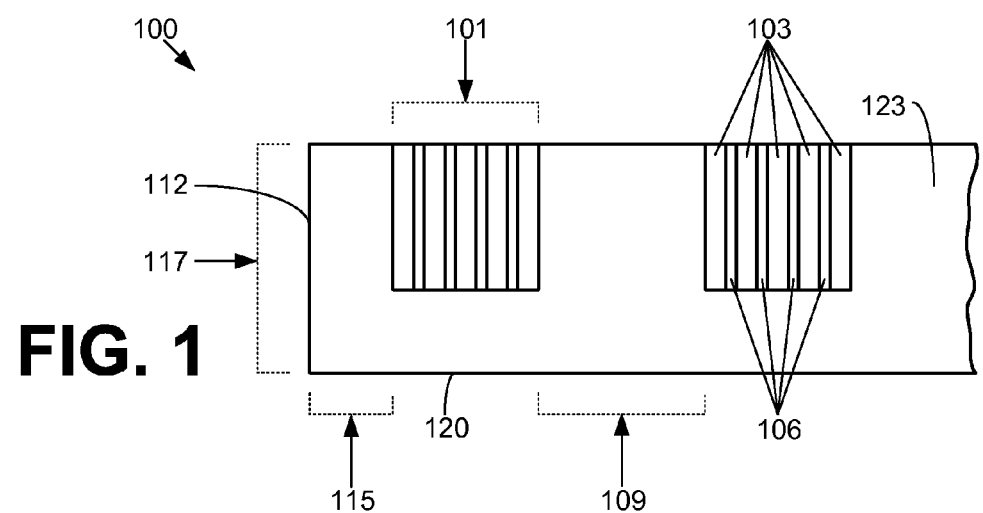
FIG. 1 is a detailed side view of a surgical instrument holder according to various embodiments.

With reference to FIG. 1, shown is a detailed side view of a surgical instrument holder 100 according to various embodiments. The surgical instrument holder 100 comprises at least one grouping 101 of slots 103, or grooves, adapted to receive and hold in a fixed position handles or other components of various surgical instruments, such as clamps, scalpels, scissors, and other surgical instruments. While the slots 103 are shown as parallel to the lateral axis of the surgical instrument holder 100, this is merely one example. In another embodiment, the slots 103 may be oriented diagonally.

The surgical instrument holder 100 may be formed of a material such as Styrofoam or some other hard foam, plastic such as polyethylene, rubber, paper, metal, or another suitable material. In one embodiment, the surgical instrument holder 100 is formed of stainless steel and configured to be sterilized in an autoclave along with any contained surgical instruments in a sterilization tray. The surgical instrument holder 100 may be solid in some embodiments and hollow in other embodiments. If the surgical instrument holder 100 is hollow, it may be preferred to form the surgical instrument holder 100 out of a rigid material, such as plastic or another rigid material.

The surgical instrument holder 100 may be distributed as a sterile and disposable unit, or may be reusable and constructed of a material capable of sterilization, e.g., stainless steel. The surgical instrument holder 100 may also be recyclable in some embodiments. The surgical instrument holder 100 may be packaged as a separate unit or as a part of a surgical package.

Each grouping 101 of slots 103 may be divided by a plurality of separators 106. The separators 106 may be formed of the same or different material than the rest of the surgical instrument holder 100, such as foam, plastic, etc. In one embodiment, each grouping 101 of slots 103 comprises five slots 103 divided by four separators 106. However, a grouping 101 of slots 103 may comprise some other number or numbers of slots 103 in other embodiments. In one embodiment, a slot 103 is ⅛ inch wide and a separator 106 is 1/16 inch wide, though the widths may vary in other embodiments in order to receive instruments of varying widths. Additionally, if the surgical instrument holder 100 is constructed out of a foam or other suitable material, slots 103 may be expanded by pressure or cutting out of the material. If the surgical instrument holder 100 is hollow, the slots 103 may be openings into the interior of the hollow surgical instrument holder 100, or the slots 103 may be bounded by material (e.g., of the separators 106) along the depth of the slots 103.

In one embodiment, a surgical instrument holder 100 may comprise ten groupings 101 of slots 103, adapted to receive fifty surgical instruments in total, though the total number of groupings 101 of slots 103 may vary in other embodiments. In various embodiments, each grouping 101 of slots 103 may be separated by a separation distance 109. As a non-limiting example, the separation distance may be one inch. The separation distance 109 may be selected based on preventing contamination of groups of instruments, the length of the instruments being used, and other factors.

By having a grouping 101 of some number of slots 103, users can easily count the number of instruments in one or multiple groupings 101. Additionally, the order of the instruments stored in the slots 103 of a grouping 101 may be important. Moreover, certain types of instruments may be arranged in one grouping 101 versus another grouping 101. Thus, the groupings 101 of slots 103 may be used to maintain logical groupings of instruments if desired. Depending on the material of the surgical instrument holder 100, the surgical instrument holder 100 may be divided into two or more pieces for convenience and grouping ability.

The surgical instrument holder 100 may have a first end surface 112 separated from a grouping 101 by an end separation distance 115 of, as a non-limiting example, ½ inch. The first end surface 112 may also be associated with a height 117. As a non-limiting example, the height 117 may be 1 and ¼ inches.

The surgical instrument holder 100 may have a base surface 120 and a top surface 123. In various embodiments, the base surface 120 may have an adhesive backing, suction mechanism, or another securing mechanism used to secure the surgical instrument holder 100 to a table surface. A securing mechanism such as an adhesive backing may be needed, for example, if the surgical instrument holder 100 is constructed of a lightweight material.

Figure 2:
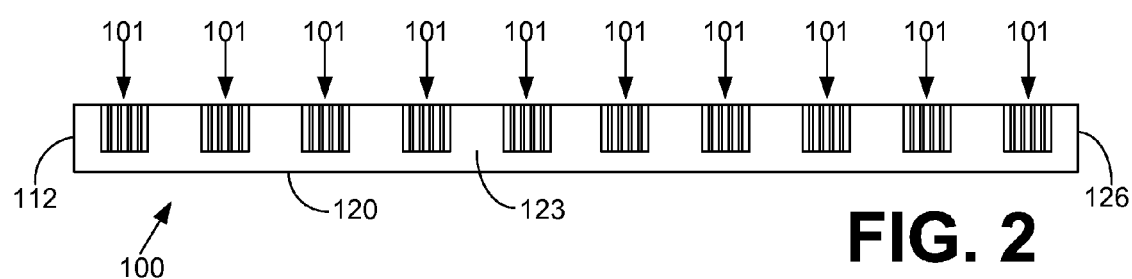
FIG. 2 is a side view of the surgical instrument holder according to various embodiments.
Figure 3:
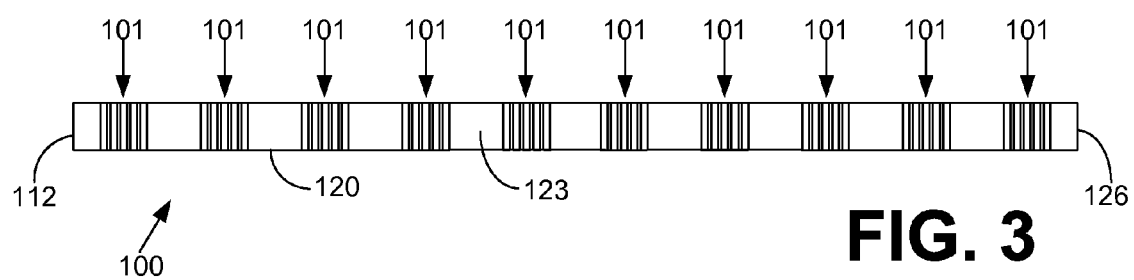
FIG. 3 is a top view of the surgical instrument holder according to various embodiments.

Referring next to FIG. 2, shown is a side view of the surgical instrument holder 100 (FIG. 1) according to various embodiments. In particular, the surgical instrument holder 100 has a first end surface 112 (FIG. 1) and a second end surface 126. As depicted in this non-limiting example, the surgical instrument holder 100 has ten groupings 101 (FIG. 1) of slots 103 (FIG. 1). The overall length of the depicted surgical instrument holder 100 may be, for example, 18 and ¾ inches or longer. FIG. 3 depicts a top view of this example of a surgical instrument holder 100 (FIG. 1).

Figure 4:
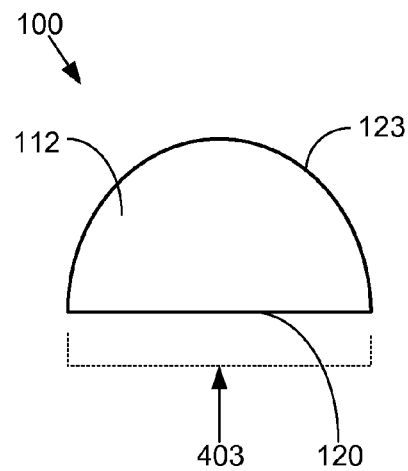
FIG. 4 is an end view of the surgical instrument holder according to various embodiments.

Moving now to FIG. 4, shown is an end view of the surgical instrument holder 100 (FIG. 1) according to various embodiments. The first end surface 112 (FIG. 1) is depicted as a semicircle. In other embodiments, the first end surface 112 may appear as an elongated semi-circle, a semi-ellipse, a polygon, or some other shape. The first end surface 112 is associated with a base width 403. The second end surface 126 (FIG. 2) may be identical to the first end surface 112. The first end surface 112 may be perpendicular to the base surface 120 (FIG. 1).

Figure 5:
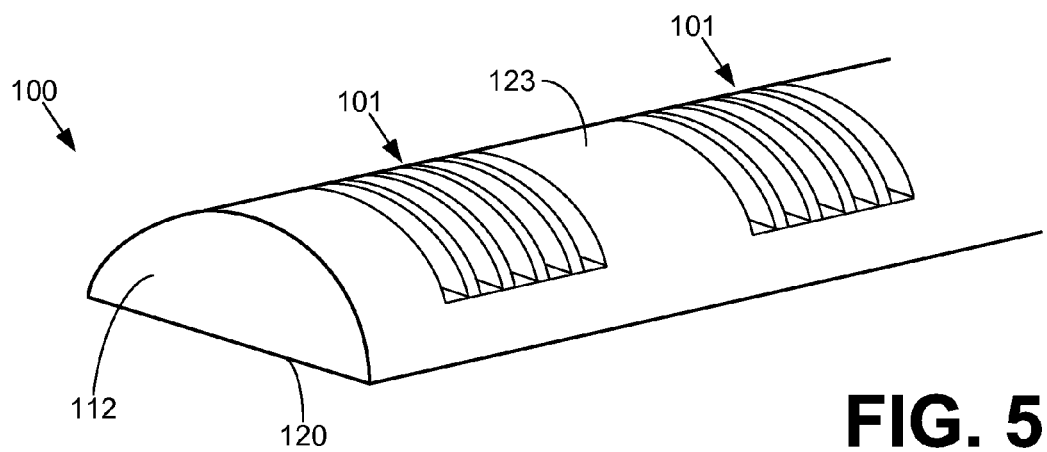
FIG. 5 is a perspective view of the surgical instrument holder according to various embodiments.

Turning now to FIG. 5, depicted is a perspective view of the surgical instrument holder 100 (FIG. 1) according to various embodiments. As illustrated, the surgical instrument holder 100 is adapted to receive surgical instruments in each grouping 101 (FIG. 1) of slots 103 (FIG. 1) and to maintain the surgical instruments in an organized and accessible condition.

In various embodiments, the surgical instrument holder 100 may be severable. As non-limiting examples, the surgical instrument holder 100 may be distributed in an extra long form or in a roll form. The surgical instrument holder 100 may be severed by cutting it, for example, with scissors, a knife, or by some other cutting tool. In one embodiment, the surgical instrument holder 100 may be severed by breaking or snapping it. To facilitate severing, the surgical instrument holder 100 may include lines or other indications showing a user where the surgical instrument holder 100 may be cut or broken along a lateral axis into two surgical instrument holders 100. The surgical instrument holder 100 may be manufactured, for example, with indents or partial cuts to ease breaking or fracturing.

In various embodiments, the surgical instrument holder 100 may contain a magnetic strip in order to facilitate secure retention of the surgical instruments contained by the surgical instrument holder.

Figure 6:
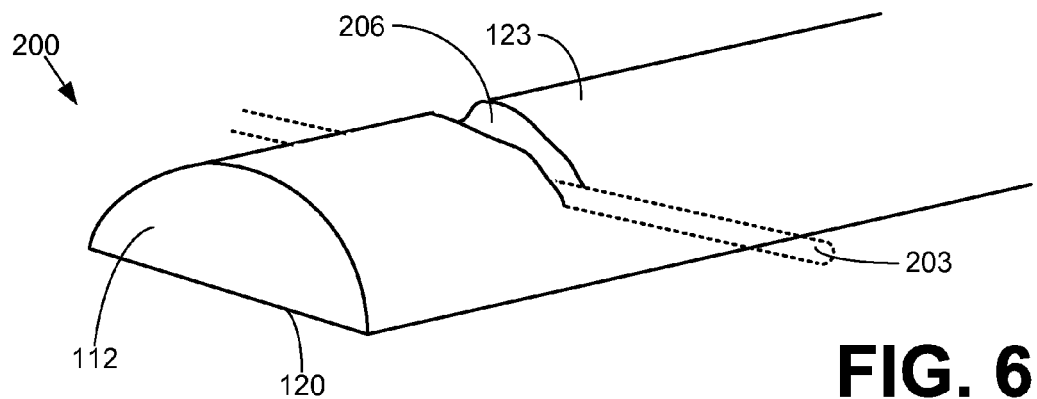
FIGS. 6 and 7 are perspective views of surgical instrument holders according to alternative embodiments.

Referring next to FIG. 6, shown is an alternative embodiment of a surgical instrument holder 200. In contrast to the surgical instrument holder 100 (FIG. 1), the surgical instrument holder 200 includes no slots. However, the surgical instrument holder 200 is formed of a material that is configured to deform under the weight of a surgical instrument 203 or another weight applied thereto. The deformation produces an indentation 206 so as to limit movement of the surgical instrument 203. At least a portion of the surgical instrument holder 200 may be formed, for example, of a non-rigid foam material. In one embodiment, the material may be non-resilient, resulting in a permanent deformation of the material. In another embodiment, the material may be resilient, resulting in only a temporary deformation of the material. In one embodiment, indications such as lines may be provided on the surgical instrument holder 200 to show proper placement of a surgical instrument 203 or to define logical groupings of surgical instruments 203.

Figure 7:
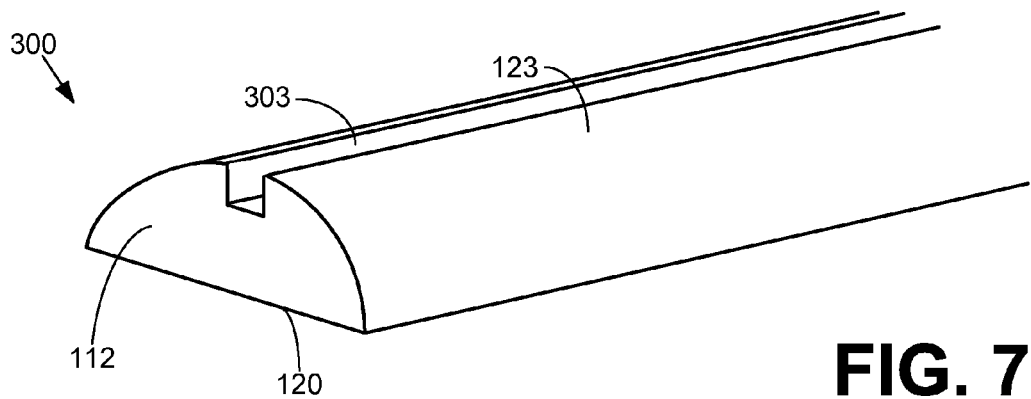

With reference to FIG. 7, shown is another alternative embodiment of a surgical instrument holder 300. In contrast to the surgical instrument holder 100 (FIG. 1) and the surgical instrument holder 200 (FIG. 6), the surgical instrument holder 300 has one slot 303 running lengthwise. The slot 303 may be used to retain any number of surgical instruments in a fixed position.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A surgical instrument holder, comprising:
    an elongated body portion being formed of a foam material and including a plurality of slots, each of the slots being configured so as to retain a surgical instrument in a fixed position, the elongated body portion having a base surface configured to contact a table surface, the elongated body portion being a semi-ellipse in cross-section outside of each slot; and wherein the slots are arranged into a plurality of groupings, each of the groupings includes a plurality of the slots, each of the slots that are adjacent within each of the groupings are separated by a first distance, each of the groupings that are adjacent are separated by a second distance, and the first distance is less than the second distance.

2. The surgical instrument holder of claim 1, wherein the base surface adjoins a top surface at a first edge and a second edge.

3. The surgical instrument holder of claim 1, wherein the elongated body portion has two lines of symmetry.

4. The surgical instrument holder of claim 1, wherein the base surface is configured to resist movement along the table surface when contacting the table surface.

5. The surgical instrument holder of claim 1, wherein the base surface is substantially flat.

6. The surgical instrument holder of claim 1, wherein the elongated body portion is solid.

7. The surgical instrument holder of claim 1, wherein at least a portion of the elongated body portion is hollow.

8. The surgical instrument holder of claim 1, wherein the elongated body portion is severable into a plurality of separate surgical instrument holders.

9. The surgical instrument holder of claim 1, further comprising packaging configured to envelop the elongated body portion and maintain a sterile environment.

10. The surgical instrument holder of claim 1, wherein the base surface includes an adhesive material.

11. The surgical instrument holder of claim 1, further comprising a magnetic strip within the elongated body portion configured to provide magnetic retention of the surgical instrument.

12. The surgical instrument holder of claim 1, wherein each of the groupings includes an equal number of the slots.

13. A surgical instrument holder, comprising:
an elongated body portion including a plurality of slots, each of the slots being configured so as to retain a surgical instrument in a fixed position, the elongated body portion having a base surface configured to contact a table surface, the elongated body portion being a semi-ellipse in cross-section outside of each slot;
a magnetic strip within the elongated body portion configured to provide magnetic retention of the surgical instrument; and
wherein the slots are arranged into a plurality of groupings, each of the groupings includes a plurality of the slots, each of the slots that are adjacent within each of the groupings are separated by a first distance, each of the groupings that are adjacent are separated by a second distance, and the first distance is less than the second distance.

14. The surgical instrument holder of claim 13, wherein the base surface adjoins a top surface at a first edge and a second edge.

15. The surgical instrument holder of claim 13, wherein the elongated body portion has two lines of symmetry.

16. The surgical instrument holder of claim 13, wherein the base surface is configured to resist movement along the table surface when contacting the table surface.

17. The surgical instrument holder of claim 13, wherein the base surface is substantially flat.

18. The surgical instrument holder of claim 13, wherein the elongated body portion is solid.

19. The surgical instrument holder of claim 13, wherein at least a portion of the elongated body portion is hollow.

20. The surgical instrument holder of claim 13, wherein the elongated body portion is formed of a foam material.

21. The surgical instrument holder of claim 13, wherein the elongated body portion is formed of a material selected from the group consisting of: plastic, rubber, paper, and metal.

22. The surgical instrument holder of claim 13, wherein the elongated body portion is severable into a plurality of separate surgical instrument holders.

23. The surgical instrument holder of claim 13, further comprising packaging configured to envelop the elongated body portion and maintain a sterile environment.

24. The surgical instrument holder of claim 13, wherein the base surface includes an adhesive material.

25. The surgical instrument holder of claim 13, wherein each of the groupings includes an equal number of the slots.

26. A surgical instrument holder, comprising:
an elongated body portion being formed of a foam material and including a plurality of slots, each of the slots being configured so as to retain a surgical instrument in a fixed position, the elongated body portion having a base surface configured to contact a table surface;
a magnetic strip within the elongated body portion configured to provide magnetic retention of the surgical instrument; and
wherein the slots are arranged into a plurality of groupings, each of the groupings includes a plurality of the slots, each of the slots that are adjacent within each of the groupings are separated by a first distance, each of the groupings that are adjacent are separated by a second distance, and the first distance is less than the second distance.

27. The surgical instrument holder of claim 26, wherein the base surface adjoins a top surface at a first edge and a second edge.

28. The surgical instrument holder of claim 26, wherein the elongated body portion has two lines of symmetry.

29. The surgical instrument holder of claim 26, wherein the base surface is configured to resist movement along the table surface when contacting the table surface.

30. The surgical instrument holder of claim 26, wherein the base surface is substantially flat.

31. The surgical instrument holder of claim 26, wherein the elongated body portion is solid.

32. The surgical instrument holder of claim 26, wherein at least a portion of the elongated body portion is hollow.

33. The surgical instrument holder of claim 26, further comprising packaging configured to envelop the elongated body portion and maintain a sterile environment.

34. The surgical instrument holder of claim 26, wherein each of the groupings includes an equal number of the slots.

* * * * *